United States Patent [19]

Siegel et al.

[11] Patent Number: 4,761,251

[45] Date of Patent: Aug. 2, 1988

[54] PROCESS FOR THE PREPARATION OF VINYLPHOSPHONIC DICHLORIDE

[75] Inventors: Herbert Siegel; Erwin Weiss, both of Hofheim am Taunus; Harald Berger, Kelkheim, all of Fed. Rep. of Germany

[73] Assignee: Hoechst Aktiengesellschaft, Frankfurt am Main, Fed. Rep. of Germany

[21] Appl. No.: 89,964

[22] Filed: Aug. 27, 1987

[30] Foreign Application Priority Data

Aug. 30, 1986 [DE] Fed. Rep. of Germany ....... 3629577

[51] Int. Cl.$^4$ ............................................. C07F 9/42
[52] U.S. Cl. ......................... 260/543 P; 260/502.4 R
[58] Field of Search ..................................... 260/543 P

[56] References Cited

U.S. PATENT DOCUMENTS 3,950,413  4/1976  Finke et al. ..................... 260/543 P

FOREIGN PATENT DOCUMENTS 1568945  7/1970  Fed. Rep. of Germany .
1162899  8/1969  United Kingdom ............ 260/543 P

*Primary Examiner*—Paul J. Killos

[57] ABSTRACT

The invention relates to a process for the preparation of vinylphosphonic dichloride through elimination of hydrogen chloride from 2-chloroethanephosphonic dichloride in the presence of catalysts. The catalysts used are tertiary phosphines, quaternary ammonium or phosphonium salts or alkali metal or alkaline-earth metal halides. When triphenyl phosphine is used as the catalyst, the reaction is carried out under reduced pressure at a temperature of 130° to 166° C. and the vinylphosphonic dichloride produced is simultaneously removed by distillation under reduced pressure. When the other catalysts are used, the process can be carried out at atmospheric pressure or reduced pressure and at temperatures of about 130° to 220° C. and the vinylphosphonic dichloride produced can be removed by distillation simultaneously with or subsequent to the reaction.

5 Claims, No Drawings

PROCESS FOR THE PREPARATION OF VINYLPHOSPHONIC DICHLORIDE

The invention relates to a process for the preparation of vinylphosphonic dichloride through elimination of hydrogen chloride from 2-chloroethanephosphonic dichloride in the presence of a catalyst. From vinylphosphonic dichloride, vinylphosphonic acid, which is an important intermediate in the preparation of flameproofing agents and an important monomer in the preparation of homo- and copolymers, is obtained through hydrolysis. Such polymers are important in paints, plastics, corrosion inhibitors and coating agents.

German Offenlegungsschrift No. 1,568,945 discloses that vinylphosphonic dichloride can be prepared from 2-chloroethanephosphonic dichloride in the presence of triphenyl phosphine as catalyst. However, temperatures above 166° C., i.e. the boiling point of vinylphosphonic dichloride, are required in this process; in fact, temperatures of about 200° C. are preferred.

Surprisingly, it has been found that this reaction also proceeds at a lower temperature if it is carried out at reduced pressure and the reaction product is continuously removed by distillation.

The invention therefore relates to a process for the preparation of vinylphosphonic dichloride through elimination of hydrogen chloride from 2-chloroethanephosphonic dichloride in the presence of triphenyl phosphine as catalyst, wherein the reaction is carried out under reduced pressure at a temperature of 130° to 166° C. and the vinylphosphonic dichloride produced is simultaneously removed by distillation.

The amount of triphenyl phosphine is generally 0.1 to 10 mole-percent, preferably 0.5 to 2 mole-percent, relative to 2-chloroethanephosphonic dichloride employed.

It has furthermore been found that other tertiary phosphines, and also quaternary ammonium or phosphonium salts or alkali metal or alkaline-earth metal halides can be used in place of triphenyl phosphine as catalysts.

The invention therefore furthermore relates to a process for the preparation of vinylphosphonic dichloride through elimination of hydrogen chloride from 2-chloroethanephosphonic dichloride in the presence of a catalyst, wherein the reaction is carried out in the presence of a catalyst which contains at least one of the following substances:

(a) tertiary phosphines of the general formula

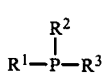

in which the radicals $R^1$, $R^2$ and $R^3$ may be identical or different and denote straight-chain or branched $C_1$–$C_{10}$-alkyl, optionally substituted by $C_1$–$C_4$-alkoxy, $C_1$–$C_4$-alkylthio or $C_1$–$C_4$-dialkylamino radicals, or denote phenyl which is substituted by halogen, $C_1$–$C_4$-alkyl or $C_1$–$C_4$-alkoxy radicals, (b) quaternary ammonium or phosphonium salts of the general formula

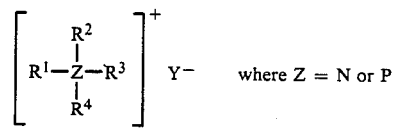

where $Y^{31}$ is an anion of a strong acid and in which $R^1$, $R^2$ and $R^3$ have the meaning mentioned in the case of (a) and $R^4$ denotes straight-chain or branched $C_1$–$C_{10}$-alkyl, or benzyl which is substituted by halogen, $C_1$–$C_4$-alkyl or $C_1$–$C_4$-alkoxy radicals, (c) alkali metal or alkaline-earth metal halides, and the vinylphosphonic dichloride produced is simultaneously or subsequently removed by distillation.

$R^1$, $R^2$ and $R^3$ are preferably $C_1$–$C_4$-alkyl radicals (optionally substituted as specified above) or phenyl radicals which are substituted in the abovementioned fashion. $R^4$ is preferably a $C_1$–$C_4$-alkyl radical or a benzyl radical which is substituted in the abovementioned fashion.

The reaction temperature is generally 130° to 220° C., preferably 140° to 190° C. The amount of catalyst is 0.1 to 10 mole-percent, preferably 0.5 to 2 mole-percent, relative to 2-chloroethanephosphonic dichloride employed.

The following tertiary phosphines are particularly suitable as catalysts:
tris(4-fluorophenyl) phosphine, tris(4-tolyl) phosphine, tris(4-methoxyphenyl) phosphine,
(N,N-diethyl)aminomethyldiphenyl phosphine, tri-n-butyl phosphine and bis(4-methoxyphenyl)methyl phosphine.

Suitable anions $Y^-$ of a strong acid in the formula for the equaternary ammonium or phosphonium salts are, for example, $Cl^-$, $Br^-$, $I^-$, $NO_3^-$, $SO_4^=$, $HSO_4^-$ and $PO_4^\equiv$, i.e. the symbol $Y^-$ shall also represent polyvalent anions.

Amongst the quaternary ammonium and phosphonium salts, those which are used in phase-transfer catalysis, for example tetrabutylammonium bromide, tetrabutylphosphonium bromide, tetrabutylammonium hydrogen sulfate, methyltrioctylammonium chloride, benzyltrimethylammonium bromide and benzyltriethylammonium chloride, are particularly suitable as catalysts. Tetrabutylammonium bromide and tetrabutylphosphonium bromide are particularly suitable.

The following examples are intended to illustrate the invention:

EXAMPLE 1

1,745.7 g (9.62 mol) of 2-chloroethanephosphonic dichloride were heated to 140° C. in the presence of 40.7 g (0.15 mol) of triphenyl phosphine, vigorous evolution of hydrogen chloride setting in. The reaction flask was evacuated to 333–400 mbar, and the vinylphosphonic dichloride produced was removed by distillation at 101°–107° C. within 2 hours. Towards the end of the reaction, the mixture was heated to 160° C., and the remaining vinylphosphonic dichloride was obtained at 60° C. and 147 mbar. The yield of vinylphosphonic dichloride was 1,205.0 g (8.32 mol, 86% of theory), at a purity of higher than 98% according to $^1$H NMR.

EXAMPLE 2

153 g (0.84 mol) of 2-chloroethanephosphonic dichloride were heated to 186° C. within one hour in the presence of 5.4 g (0.017 mol) of tetrabutylammonium bromide. The reaction mixture was subsequently kept at 186°–200° C. for one hour, vinylphosphonic dichloride distilling over to a receiver via a column at 167°–168° C. in an amount of 106.5 g (0.73 mol, 87% of theory).

EXAMPLE 3

Analogously to Example 2, 149.7 g (0.825 mol) of chloroethanephosphonic dichloride were heated to 186° C. within 25 minutes in the presence of 5.3 g (0.016 mol) of tetrabutylphosphonium bromide. The reaction mixture was subsequently kept at 186°–200° C. for one hour, 97.9 g (0.676 mol, 82% of theory) of vinylphosphonic dichloride distilling over at 165°–166° C. via a column.

EXAMPLE 4

Analogously to Example 2, 151.2 g (0.83 mol) of chloroethanephosphonic dichloride were heated to 190° C. within 30 minutes in the presence of 1.5 g (0.017 mol) of lithium bromide. The reaction mixture was kept at 190°–210° C. for one hour, 98.3 g (0.68 mol, 82% of theory) of vinylphosphonic dichloride distilling over at 166°–167° C. via a column.

We claim:

1. A process for the preparation of vinylphosphonic dichloride through elimination of hydrogen chloride from 2-chloroethanephosphonic dichloride in the presence of triphenyl phosphine as catalyst, wherein the reaction is carried out under reduced pressure at a temperature of 130° to 166° C. and the vinylphosphonic dichloride produced is simultaneously removed by distillation.

2. A process for the preparation of vinylphosphonic dichloride through elimination of hydrogen chloride from 2-chloroethanephosphonic dichloride in the presence of a catalyst, wherein the reaction is carried out in the presence of a catalyst which contains at least one of the following substances:

(a) tertiary phosphines of the formula

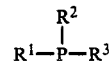

in which the radicals $R^1$, $R^2$ and $R^3$ may be identical or different and denote straight-chain or branched $C_1$–$C_{10}$-alkyl, optionally substituted by $C_1$–$C_4$-alkoxy, $C_1$–$C_4$-alkylthio or $C_1$–$C_4$-dialkylamino radicals, or denote phenyl which is substituted by halogen, $C_1$–$C_4$-alkyl or $C_1$–$C_4$-alkoxy radicals, (b) quaternary ammonium or phosphonium salts of the formula

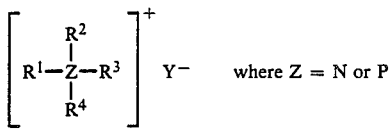

$Y^-$ where $Z = N$ or $P$
where
$Y^-$ is an anion of a strong acid and in which $R^1$, $R^2$ and $R^3$ have the meaning mentioned in the case of (a) and
$R^4$ denotes straight-chain or branched $C_1$–$C_{10}$-alkyl, or benzyl which is substituted by halogen, $C_1$–$C_4$-alkyl or $C_1$–$C_4$-alkoxy radicals, (c) alkali metal or alkaline-earth metal halides, and the vinylphosphonic dichloride produced is simultaneously or subsequently removed by distillation.

3. The process as claimed in claim 2, wherein it is carried out at a temperature of 130° to 220° C.

4. The process as claimed in claim 2, wherein it is carried out at a temperature of 140° to 190° C.

5. The process as claimed in claim 2, wherein the catalyst employed is tetrabutylammonium bromide, tetrabutylphosphonium bromide or lithium bromide.

* * * * *